(12) United States Patent
Wu et al.

(10) Patent No.: US 9,198,288 B2
(45) Date of Patent: Nov. 24, 2015

(54) METHOD OF MAKING SILVER CARBOXYLATES FOR CONDUCTIVE INK

(71) Applicant: XEROX CORPORATION, Norwalk, CT (US)

(72) Inventors: Yiliang Wu, Oakville (CA); Ping Liu, Mississauga (CA)

(73) Assignee: XEROX CORPORATION, Norwalk, CT (US)

( * ) Notice: Subject to any disclaimer, the term of this patent is extended or adjusted under 35 U.S.C. 154(b) by 213 days.

(21) Appl. No.: 13/894,495

(22) Filed: May 15, 2013

(65) Prior Publication Data

US 2014/0342084 A1    Nov. 20, 2014

(51) Int. Cl.
| | |
|---|---|
| H05K 1/09 | (2006.01) |
| H01K 3/12 | (2006.01) |
| C07C 51/41 | (2006.01) |
| H05K 3/10 | (2006.01) |
| H05K 3/12 | (2006.01) |

(52) U.S. Cl.
CPC ............... H05K 1/09 (2013.01); C07C 51/412 (2013.01); *H05K 1/092* (2013.01); *H05K 3/105* (2013.01); *H05K 3/12* (2013.01); *H05K 2203/121* (2013.01); *H05K 2203/125* (2013.01)

(58) Field of Classification Search
CPC .................................................... C07C 51/412
See application file for complete search history.

(56) References Cited

U.S. PATENT DOCUMENTS

| | | | |
|---|---|---|---|
| 4,723,024 A * | 2/1988 | DePompei | ............ 554/71 |
| 6,942,825 B2 | 9/2005 | Honda et al. | |
| 8,057,849 B2 | 11/2011 | Liu et al. | |
| 8,158,032 B2 | 4/2012 | Liu et al. | |
| 8,298,314 B2 | 10/2012 | Li | |
| 8,324,294 B2 | 12/2012 | Wu et al. | |
| 8,361,350 B2 | 1/2013 | Wu et al. | |
| 2010/0143591 A1* | 6/2010 | Wu et al. | ............ 427/256 |
| 2010/0239750 A1 | 9/2010 | Breton et al. | |
| 2011/0135808 A1 | 6/2011 | Liu et al. | |

FOREIGN PATENT DOCUMENTS

EP    0380213 A2 *  8/1990  ............... B01J 23/38

OTHER PUBLICATIONS

U.S. Appl. No. 13/894,475, filed May 15, 2013 in the name of Wu et al.

* cited by examiner

*Primary Examiner* — Katherine A Bareford
*Assistant Examiner* — Christina McClure
(74) *Attorney, Agent, or Firm* — Pillsbury Winthrop Shaw Pittman LLP

(57) ABSTRACT

A method of making silver carboxylate includes forming a mixture of at least one carboxylic acid and at least one aromatic hydrocarbon solvent, and at room temperature, introducing silver oxide into the mixture to form the silver carboxylate in the aromatic hydrocarbon solvent. The mixture may be free of alkali bases and mineral acids, with no additional materials being introduced into the mixture when introducing the silver oxide.

12 Claims, No Drawings

METHOD OF MAKING SILVER CARBOXYLATES FOR CONDUCTIVE INK

BACKGROUND

Fabrication of electronic circuit elements using liquid deposition techniques is of profound interest as such techniques provide potentially low-cost alternatives to conventional mainstream amorphous silicon technologies for electronic applications such as thin film transistors (TFTs), light-emitting diodes (LEDs), RFID tags, photovoltaics, and the like. However the deposition and/or patterning of functional electrodes, pixel pads, and conductive traces, lines and tracks which meet the conductivity, processing, and cost requirements for practical applications have been a great challenge.

Solution processable or printable silver-based conducting materials have attracted attention for printed electronic applications. In this regard, fabrication of electronic circuit elements using silver nanoparticle ink compositions is known. Silver nanoparticle ink compositions are described in, for example, U.S. Pat. Nos. 8,361,350, 8,324,294, 8,298,314, 8,158,032, and 8,057,849, each incorporated herein by reference in its entirety.

The use of silver nanoparticle ink compositions may have some drawbacks, for example such as consistency in nanoparticle size and quality, which may negatively impact the formation of consistent and reliable conductive features and stability of the ink composition. Silver nanoparticle ink compositions can also be expensive to prepare and use.

Besides silver metal nanoparticles, another type of silver-based conductive material, silver-organic compounds, may offer several benefits such as lower-cost, better stability, and ease of preparation, when compared to silver nanoparticles with respect to use in conductive ink compositions. For example, silver carboxylates, such as silver neodecanoate, are low-cost, very stable silver salts that may be used to print conductive traces at a low processing temperature.

However, silver carboxylates such as silver neodecanoate have previously been synthesized in a two-step process, which involved expensive starting materials and required a large amount of water/methanol to remove sodium salt impurity. For example, silver carboxylate such as silver neodecanoate may be synthesized in a two-step process in which first, neodecanoic acid is reacted with an alkali base solution such as sodium hydroxide solution to form sodium neodecanoate in a water/alcohol mixture. The sodium neodecanoate then is reacted with silver nitrate to precipitate the silver neodecanoate salt, followed by washing with a large amount of water/methanol to remove the sodium salt. The drawbacks of this approach are clear: 1) expensive starting materials such as silver nitrate have to be used; and 2) a large amount of water/methanol is required to wash the product to remove the sodium salt impurity.

U.S. Pat. No. 4,723,024, incorporated herein by reference in its entirety, describes a method of preparing a silver salt of an organic acid comprising the steps of: (A) preparing a mixture of: (1) at least one organic carboxylic acid, (2) a hydrocarbon solvent, and (3) a mineral acid; and (B) adding a source of silver cation while maintaining the temperature of the resultant mixture at least at about 60° C. for a period of time sufficient to form the desired silver salt. The method described in this patent thus requires the use of a mineral acid and requires an elevated reaction temperature.

There remains a need for improved methods of making silver carboxylates, and conductive ink compositions comprised of silver carboxylates that are capable of forming high resolution traces having high conductivity, which methods are more economical than present methods.

SUMMARY

The above and other issues are addressed by the present application, wherein in embodiments, the application relates to a method of making silver carboxylate, comprising forming a mixture of at least one carboxylic acid and at least one aromatic hydrocarbon solvent, and at room temperature, introducing silver oxide into the mixture to form the silver carboxylate in the aromatic hydrocarbon solvent.

Also described herein is a method of making silver carboxylate, comprising forming a mixture of at least one carboxylic acid and at least one aromatic hydrocarbon solvent, and the mixture being free of alkali bases and of mineral acids, and introducing silver oxide into the mixture to form the silver carboxylate in the aromatic hydrocarbon solvent.

Further described is a method of forming conductive features on a substrate, the method comprising forming a silver carboxylate composition comprised of silver carboxylate in an aromatic hydrocarbon solvent by forming a mixture of at least one carboxylic acid and at least one aromatic hydrocarbon solvent, and at room temperature, introducing silver oxide into the mixture to form the silver carboxylate composition, depositing the silver carboxylate composition onto the substrate to form deposited features, and heating the deposited features on the substrate to a temperature from about 80° C. to about 200° C. to form conductive silver features on the substrate.

EMBODIMENTS

In this specification and the claims that follow, singular forms such as "a," "an," and "the" include plural forms unless the content clearly dictates otherwise. All ranges disclosed herein include, unless specifically indicated, all endpoints and intermediate values. In addition, reference may be made to a number of terms that shall be defined as follows:

"Optional" or "optionally" refer, for example, to instances in which subsequently described circumstances may or may not occur, and include instances in which the circumstance occurs and instances in which the circumstance does not occur.

The phrases "one or more" and "at least one" refer, for example, to instances in which one of the subsequently described circumstances occurs, and to instances in which more than one of the subsequently described circumstances occurs.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

Described herein is a facile method to prepare silver carboxylates by directly reacting a carboxylic acid with silver oxide in a solvent at room temperature. This method has several advantages over prior methods discussed above: 1) the reaction mixture is free of alkali bases and free of mineral acids, and thus no impurity ions are retained in the silver carboxylate product; 2) a low-cost starting material, silver oxide, is used; 3) the method utilizes a single-step, mild reaction, which can reduce the overall processing cost and eliminate the need for washing or purification of the silver carboxylate product.

The methods herein thus employ a reaction mixture that is desirably comprised of only the carboxylic acid component, silver oxide and solvent. To the extent that other materials are desired to be included in the reaction mixture, the reaction mixture should still remain free of alkali bases and mineral acids.

As the solvent of the reaction mixture, a solvent that can dissolve the silver carboxylate product at a high concentration is to be used. The concentration of the silver carboxylate in the solvent is desirably at least 10% by weight, or at least 20% by weight, or at least 30% by weight including at least 40% by weight. In a given reaction, substantially all of the silver carboxylate produced in the reaction should be dissolved in the solvent of the reaction mixture. This enables the reaction to proceed with a high conversion rate of the silver oxide into the silver carboxylate products. The solvent should also have good solubility with the carboxylic acid of the reaction mixture.

In embodiments, the solvent is an aromatic hydrocarbon solvent, such as one of or a combination of toluene, xylene, trimethylbenzene such as 1,2,4-trimethylbenzene and 1,3,5-trimethylbenzene, ethylbenzene, diethylbenzene, tetrahydronaphthalene, methylnaphthalene, propylbenzene, butylbenzene, methyl propylbenzene and cumene.

The solvent may be present in the reaction mixture in an amount of, for example from about 30% to about 90%, including from about 30% to about 80% or from about 35% to about 70% by weight of the reaction mixture.

The carboxylic acid of the reaction mixture may be one or more carboxylic acids, and may be aliphatic, cycloaliphatic and aromatic monobasic and polybasic carboxylic acids. The carboxylic acid(s) may be linear or branched and have from 6 to 28 carbon atoms, such as from 8 to 20 carbon atoms or from 8 to 16 carbon atoms. The use of carboxylic acids with fewer than 6 total carbon atoms may result in silver carboxylates that have solubility issues in the solvent, while the use of carboxylic acids with more than 28 total carbon atoms may result in too much organic material being present in the silver carboxylate, making it difficult to achieve high conductivity.

Examples of suitable carboxylic acids for the reaction mixture include straight chain carboxylic acids such as octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, icosanoic acid and the like, and branched chain carboxylic acids such as neodecanoic acid. In embodiments, a liquid carboxylic acid at room temperature is preferred.

The carboxylic acid may be present in the reaction mixture in an amount of, for example, from about 10% to about 60%, including from about 20% to about 60% or from about 30% to about 60% by weight of the reaction mixture. In embodiments, the carboxylic acid component is present in the reaction mixture in an amount that is substantially equimolar with the amount of silver oxide to be added to the reaction mixture. In other embodiments, the molar ratio of carboxylic acid component to the silver oxide in the reaction mixture is from about 1:1 to about 3:1, including from about 1:1 to about 2:1.

As the silver oxide of the reaction mixture, silver oxide ($Ag_2O$) powder may be used. Silver oxide with any particle size can be used. In embodiments, the silver oxide is micro-sized (1 micron or more in average diameter) particles. In other embodiments, the silver oxide is submicron sized (less than 1 micron in average diameter).

The silver oxide may be present in the reaction mixture in an amount of, for example from about 2% to about 60%, including from about 5% to about 60% by weight of the reaction mixture.

In the method of making the silver carboxylate, the reaction mixture is first formed. In making the reaction mixture, the components of the reaction mixture may be added in any order. In embodiments, the carboxylic acid is added to the solvent, and the silver oxide is subsequently added to the solvent in an incremental manner. The term "incremental" or "incrementally" means that the silver oxide is added slowly over time into the reaction mixture at a substantially constant rate, so that the reaction mixture has a substantially low solid component. In embodiments, the solid component (the silver oxide) in the reaction mixture is less than 15% including less than 10%, or less than 5% by weight. The incremental addition and the total amount are controlled to ensure the formation of silver carboxylate compound and reduce the possibility of forming silver nanoparticles during the reaction.

The reaction is conducted at room temperature, for example a temperature of from about 23° C. to about 27° C., and it is thus not necessary to subject the reaction mixture to heating. The reaction mixture may optionally be subjected to stirring or other mixing action to assist in dissolution of the silver oxide in the solvent and to assist in driving the reaction.

In the reaction, the carboxylic acid directly reacts with the silver oxide, generating silver carboxylate and water. The generated water may be removed from the reaction product in any suitable manner. A solution of the silver carboxylate in the solvent is thus obtained. The solution may comprise from about 10% to about 60% by weight silver carboxylate, such as from about 20% to about 50% by weight silver carboxylate.

The obtained solution of silver carboxylate in the solvent may be used directly as obtained from the reaction as a conductive ink or other material for deposition. Alternatively, the silver carboxylate may be isolated from the solvent by precipitation using a non-solvent such as methanol, ethanol, propanol, acetone, acetonitrile, and the like, and the isolated silver carboxylate re-dissolved in a suitable vehicle to form a conductive ink or other material for deposition.

The fabrication of conductive features, such as an electrically conductive element, from the silver carboxylate composition can be carried out by depositing the composition on a substrate using any suitable liquid deposition technique at any suitable time prior to or subsequent to the formation of other optional layer or layers on the substrate. Thus, liquid deposition of the composition on the substrate can occur either on a substrate or on a substrate already containing layered material, for example, a semiconductor layer and/or an insulating layer.

"Liquid deposition" refers to, for example, deposition of the composition using a liquid process such as printing or liquid coating, where the liquid is the silver carboxylate composition. The silver carboxylate composition may be referred to as an ink when it is used in an inkjet printer or similar printing device to be deposited on a substrate. Examples of liquid coating processes may include, for example, spin coating, blade coating, rod coating, dip coating, and the like. Examples of printing techniques may include, for example, lithography or offset printing, gravure, flexography, screen printing, stencil printing, inkjet printing, stamping (such as microcontact printing), and the like. Liquid deposition deposits a layer or line of the composition having a thickness ranging from about 5 nanometers to about 5 millimeters, such as from about 10 nanometers to about 1000 micrometers on the substrate. The deposited silver carboxylate composition at this stage may or may not exhibit appreciable electrical conductivity.

The substrate upon which the silver metal features are deposited may be any suitable substrate, including, for example, silicon, glass plate, plastic film, sheet, fabric, or paper. For structurally flexible devices, plastic substrates, such as for example polyester, polycarbonate, polyimide sheets and the like may be used. The thickness of the substrate may be from amount 10 micrometers to over 10 millimeters with an exemplary thickness being from about 50 micrometers to about 2 millimeters, especially for a flexible plastic substrate and from about 0.4 to about 10 millimeters for a rigid substrate such as glass or silicon.

Heating the deposited composition at a temperature of, for example, at or below about 250° C., such as, for example, from about 80° C. to about 200° C., from about 80° C. to about 180° C., from about 80° C. to about 160° C., from about 100° C. to about 140° C., "anneals" the composition to reduce the silver carboxylate and form an electrically conductive feature. Upon heating, the silver carboxylate undergoes a self-reduction to form silver nanoparticles, while the organic component is evaporated. The heating temperature is one that does not cause adverse changes in the properties of previously deposited layer(s) or the substrate (whether single layer substrate or multilayer substrate). Also, the low heating temperatures described above allows the use of low cost plastic substrates, which have an annealing temperature below 200° C.

The heating can be performed for a time ranging from, for example, 0.01 second to about 10 hours and from about 10 seconds to 1 hour. The heating can be performed in air, in an inert atmosphere, for example, under nitrogen or argon, or in a reducing atmosphere, for example, under nitrogen containing from 1 to about 20 percent by volume hydrogen. The heating can also be performed under normal atmospheric pressure or at a reduced pressure of, for example, from about 1000 mbars to about 0.01 mbars.

As used herein, the term "heating" encompasses any technique(s) that can impart sufficient energy to the heated material or substrate to anneal the silver carboxylate. Examples of heating techniques may include thermal heating (for example, a hot plate, an oven, and a burner), infra-red ("IR") radiation, a laser beam, flash light, microwave radiation, or UV radiation, or a combination thereof.

Prior to heating, the layer of the deposited paste may be electrically insulating or with very low electrical conductivity, but heating results in an electrically conductive material.

The conductivity of the resulting element produced by heating the deposited silver carboxylate composition is, for example, more than about 100 Siemens/centimeter ("S/cm"), more than about 1000 S/cm, more than about 2,000 S/cm, more than about 5,000 S/cm, or more than about 10,000 S/cm or more than 50,000 S/cm. The resulting elements may be used as electrodes, conductive pads, interconnect, conductive lines, conductive tracks, and the like in electronic devices such as thin film transistors, organic light emitting diodes, RFID (radio frequency identification) tags, photovoltaic, displays, printed antenna and other electronic devices which require conductive elements or components.

The embodiments disclosed herein will now be described in detail with respect to specific exemplary embodiments thereof, it being understood that these examples are intended to be illustrative only and the embodiments disclosed herein is not intended to be limited to the materials, conditions, or process parameters recited herein. All percentages and parts are by weight unless otherwise indicated.

EXAMPLE 1

2.48 g (0.0144 mole) neodecanoic acid was added into 6 ml of 1,2,4-trimethylbenzene. 1.66 g (0.0072 mole) silver oxide ($Ag_2O$) powder was added slowly into the mixture over the course of 5 minutes. The black silver oxide was dissolved, and a clear solution containing about 40 wt % silver neodecanoate in 1,2,4-trimethylbenzene was obtained (reaction scheme is shown in the following) after approximately 20 minutes.

½ $Ag_2O$ (silver (I) oxide) +

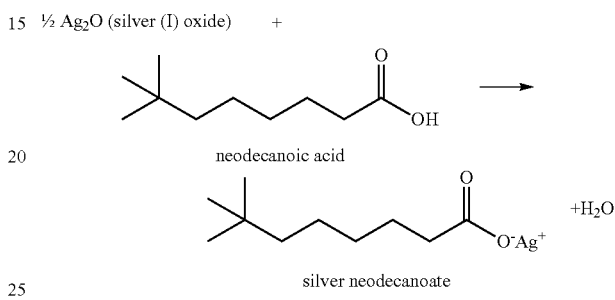

The obtained solution, without further purification, was spin coated on a glass slide and annealed at 140° C. for 20 minutes. A silver film was obtained, showing a conductivity of $2.4 \times 10^4$ S/cm as measured by standard 4-probe technique.

EXAMPLE 2

22.5 g (0.13 mole) neodecanoic acid was added into 30 ml of toluene. 10 g (0.043 mole) silver oxide ($Ag_2O$) powder was added slowly into the mixture, and stirred at room temperature for 60 minutes. The black silver oxide was dissolved to form a brown solution. 100 ml of methanol was added to the reaction mixture to precipitate the silver neodecanoate. White to light brown silver salt was collected by filtration and drying.

40 wt % clear solution of the collected silver salt was prepared by dissolving the silver neodecanoate in o-xylene at room temperature. After filtration with a 0.45 micron syringe filter, the solution was spin coated on a glass slide and annealed at 140° C. for 20 minutes. A silver film was obtained, showing a conductivity of $2.6 \times 10^4$ S/cm as measured by standard 4-probe technique.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:
1. A method of making silver carboxylate, comprising
   forming a mixture of at least one carboxylic acid and at least one aromatic hydrocarbon solvent, and
   at room temperature, incrementally introducing silver oxide into the mixture to form the silver carboxylate in the aromatic hydrocarbon solvent;
      wherein the method further comprises isolating the silver carboxylate from the aromatic hydrocarbon solvent by precipitating with a non-solvent selected from the group consisting of methanol, ethanol, propanol, acetone and acetonitrile; and wherein the silver oxide added to the mixture during the incremental introducing step is less than 15% by weight of the mixture to reduce the possibility of forming silver nanoparticles during the reaction.

2. The method according to claim 1, wherein the silver oxide comprises silver oxide powder.

3. The method according to claim 1, wherein the at least one carboxylic acid is a carboxylic acid having from 8 to 20 carbon atoms.

4. The method according to claim 3, wherein the at least one carboxylic acid is neodecanoic acid.

5. The method according to claim 1, wherein the at least one aromatic hydrocarbon solvent is selected from the group consisting of toluene, xylene, trimethylbenzene, ethylbenzene, diethylbenzene, tetrahydronaphthalene, methylnaphthalene, propylbenzene, methyl propylbenzene, butylbenzene, cumene, and combinations thereof.

6. A method of making silver carboxylate, comprising
forming a mixture of at least one carboxylic acid and at least one aromatic hydrocarbon solvent, and the mixture being free of alkali bases and of mineral acids, and
incrementally introducing silver oxide into the mixture to form the silver carboxylate in the aromatic hydrocarbon solvent;
wherein the method further comprises isolating the silver carboxylate from the aromatic hydrocarbon solvent by precipitating with non-solvent selected from the group consisting of methanol, ethanol, propanol, acetone and acetonitrile; and
wherein the silver oxide added to the mixture during the incremental introducing step is less than 15% by weight of the mixture to reduce the possibility of forming silver nanoparticles during the reaction.

7. The method according to claim 6, wherein the mixture consists of the at least one carboxylic acid and the at least one aromatic hydrocarbon solvent, and wherein no additional materials are introduced into the mixture when introducing the silver oxide.

8. The method according to claim 6, wherein the introducing is conducted at room temperature.

9. The method according to claim 6, wherein the silver oxide comprises silver oxide powder.

10. The method according to claim 6, wherein the at least one carboxylic acid is a carboxylic acid having from 8 to 20 carbon atoms.

11. The method according to claim 10, wherein the at least one carboxylic acid is neodecanoic acid.

12. The method according to claim 6, wherein the at least one aromatic hydrocarbon solvent is selected from the group consisting of toluene, xylene, 1,2,4-trimethylbenzene, ethylbenzene, diethylbenzene, tetrahydronaphthalene, methylnaphthalene, propylbenzene, methyl propylbenzene, butylbenzene, cumene and combinations thereof.

* * * * *